(12) United States Patent
Lawrence et al.

(10) Patent No.: US 6,403,363 B1
(45) Date of Patent: Jun. 11, 2002

(54) METHOD OF PRESERVATION OF VACCINES WITH POLYBIGUANIDE

(75) Inventors: Michelle Irene Gregarach Lawrence; Declan Greally, both of Liverpool (GB)

(73) Assignee: Medeva Europe Limited, London (GB)

( * ) Notice: Subject to any disclaimer, the term of this patent is extended or adjusted under 35 U.S.C. 154(b) by 0 days.

(21) Appl. No.: 09/903,935

(22) Filed: Jul. 12, 2001

Related U.S. Application Data (63) Continuation of application No. 09/381,448, filed as application No. PCT/GB98/00797 on Mar. 18, 1998.

(30) Foreign Application Priority Data

Mar. 20, 1997 (GB) ................................................ 9705740

(51) Int. Cl.[7] .................... C12N 1/04; A61K 31/74; A61K 39/295; A61K 39/145; A61K 39/155
(52) U.S. Cl. ................. 435/260; 514/635; 514/642; 424/78.04; 424/201.1; 424/202.1; 424/204.1; 424/209.1; 424/211.1; 424/210.1; 435/236
(58) Field of Search ................ 514/635, 642; 424/78.04, 201.1, 202.1, 204.1, 209.1, 211.1, 210.1; 435/236, 260

(56) References Cited

U.S. PATENT DOCUMENTS

| 3,874,999 | A | * | 4/1975 | Zaremba et al. | ............. | 195/1.5 |
| 4,654,208 | A | * | 3/1987 | Stockel et al. | ................ | 424/78 |
| 4,758,595 | A | * | 7/1988 | Obunbiyi et al. | ........... | 514/635 |
| 4,814,334 | A | | 3/1989 | Salkin | ........................ | 514/256 |

FOREIGN PATENT DOCUMENTS

| EP | 0 701 821 A1 | 3/1996 |
| GB | 984074 | 2/1965 |
| WO | WO 93/16681 | 9/1993 |
| WO | WO 94/27440 | 12/1994 |
| WO | WO 97/00076 | 1/1997 |

OTHER PUBLICATIONS

"2140. Chlorhexidine," *The Merck Index*, p. 348.

* cited by examiner

*Primary Examiner*—Hankyel T. Park
*Assistant Examiner*—Stacy S. Brown
(74) *Attorney, Agent, or Firm*—Heslin Rothenberg Farley & Mesiti P.C.; Candice J. Clement, Esq.

(57) ABSTRACT

A method for preventing or reducing bacterial contamination of a viral vaccine is disclosed. The method comprises adding an effective preserving amount of a polybiguanide-containing preservative composition to a solution containing vaccine virus or virus antigen. The method is particularly useful in preventing or reducing bacterial contamination of process solutions involved in the manufacture of influenza vaccines.

28 Claims, 5 Drawing Sheets

METHOD OF PRESERVATION OF VACCINES WITH POLYBIGUANIDE

CROSS REFERENCE TO RELATED APPLICATIONS

This application is a continuation of co-pending U.S. Pat. application Ser. No. 09/381,448, filed May 30, 2000 as a 35 USC §371 filing of PCT/GB98/00797, filed Mar. 18, 1998, and claims priority from GB 9705740.0, filed Mar. 20, 1997. The entire contents of the earlier applications is hereby incorporated by reference.

FIELD OF THE INVENTION

This invention relates to methods of preventing or reducing microbial, and in particular, bacterial, contamination of viral vaccines such as influenza vaccines, during manufacture.

BACKGROUND OF THE INVENTION

Current influenza vaccines consist of either inactivated whole virus, disrupted virus (split vaccines) or purified preparations of the membrane glycoproteins haemagglutinin (HA) and neuraminidase (NA) sub-unit vaccines. Haemagglutinin and neuraminidase are the antigens to which protective antibody responses are directed, haemagglutinin being the major protective antigen. The haemagglutinin and neuraminidase antigens may be present in the vaccine in the form of rosettes, e.g. particles with a radius in the range 10 to 25 nanometer. One example of a commercially available haemagglutinin/neuraminidase preparation is the "Fluvirin" product manufactured and sold by Evans Medical Limited of Speke, Merseyside, United Kingdom; see also S. Renfrey and A. Watts, Vaccine, 1994, Volume 12, Number 8, pp 747–752.

During the manufacture of viral vaccines such as the aforementioned influenza vaccines, preservatives can be used to reduce or prevent microbial contamination of the solutions isolated from the viral growth medium, and subsequent solutions containing partially purified or purified viral antigens. For example, with viral vaccines such as influenza vaccines in which eggs are used as the viral growth medium, a preservative can be added to the allantoic fluid harvested from the eggs after incubation with the virus. The purpose of the preservative is to reduce levels of contamination due to the inherent non-sterility of the egg, and also to reduce or prevent bacterial contamination during subsequent processing of the harvested allantoic fluid.

One preservative commonly used in vaccine production is the organo mercurial compound thiomersal, the full chemical name for which is sodium ethylmercurithiosalicylate. Thiomersal is generally effective as a preservative in vaccine production, but a major problem is that its use results in considerable quantities of mercury-containing waste being produced. In line with current and intended legislation, mercury-containing waste needs to be disposed of very carefully in order to avoid adverse effects on the environment.

In order to avoid releasing mercury-containing waste into the environment, there are several possible options. Firstly, the waste can be treated to remove mercury, and this approach is exemplified by U.S. Pat. Nos. 5,437,797 and 5,154,833. Another alternative is to discontinue the use of preservatives altogether, but a more preferable option in view of the difficulties in maintaining solution sterility in the absence of preservatives would be to find an alternative preservative which is at least as effective as thiomersal but which does not suffer from the same disposal and toxicity problems.

In order to be suitable for use in vaccine manufacture, a preservative must meet a number of very stringent criteria. Firstly, the preservative must be effective against the microbial species typically found in the vaccine production environment. Secondly, it must be compatible with the virus and the viral antigens and, if added during the viral growth phase, should not have any adverse effects on the growth of the virus in the medium. Thirdly, the preservative should be compatible with the production process and should not cause problems during the further processing of the vaccine composition. Fourthly, the preservative should be one which does not have an adverse effect on the environment, thereby minimising the need to take additional steps during its disposal.

It has now been found that the above criteria can be met using a polybiguanide preservative.

SUMMARY OF THE INVENTION

In a first aspect, the principles of the invention provide a method of preventing or reducing bacterial contamination of a viral vaccine, wherein the method comprises adding to a solution containing virus or virus antigen, an effective amount of a preservative composition containing polybiguanide.

Accordingly, in a first aspect, the invention provides a method of preventing or reducing bacterial contamination of a viral vaccine, which method comprises adding to a solution containing vaccine virus or virus antigen an effective preserving amount of a preservative composition containing polybiguanide.

In another aspect, the invention provides a preserved viral vaccine composition comprising a solution containing vaccine virus or virus antigen and an effective preserving amount of a preservative composition containing polybiguanide.

In one embodiment of the invention, the solution may be the final form of the vaccine immediately prior to or after filling into dosage containers such as vials, ampoules and the like, particularly multi-dose containers.

In another embodiment, the solution may be a process solution, the term "process solution" as used herein referring to any solution containing the vaccine virus or viral antigens derived from the vaccine virus up to the point at which the vaccine is filled into dosage containers.

Examples of "process solutions" are solutions of virus harvested from the medium in which the virus has been grown, such as the allantoic fluid from eggs, or the supernatant from a cell culture. Other examples include solutions containing disrupted virus and free antigens such as surface antigens, as well as partially purified and purified solutions of antigens. The term "process solution" can also include the viral growth medium itself, the preservative being added to the medium at the beginning of or during the growth phase of the virus.

The vaccine can contain a single strain of virus, or antigens from a single strain of virus, or it can contain a blend of antigens from different viral strains. For example, in the case of influenza vaccines, the vaccine can contain antigens from one or more strains of influenza A together with antigens from one or more strains of influenza B.

The polybiguanide is typically a polymeric compound containing the repeating unit:

—[NH—C(NH)—NH—C(NH)—NH—R]$_n$— wherein R is a divalent hydrocarbon chain, preferably having at least 2 carbon atoms; and n represents the number of repeating units and is at least 2.

More usually, n is in the range from 3 to 20, for example from 4 to about 16, preferably from 5 to 12, and more preferably from 5 to 7. The values given for n are the average values, since a given solution of a polybiguanide will frequently contain a mixture of molecules of differing chain lengths. For example, a solution of a polybiguanide can contain molecules in which n ranges from 1 to about 40. A preferred polybiguanide is one in which the average value for n is 5.5.

The molecular weight of the polymer, excluding the weight of any acid present in the form of acid addition salts of the polymer, may be up to 12,000 or more but is usually less than 5000, and is preferably in the range from about 750 to about 3000.

A presently preferred polybiguanide is poly (hexamethylene) biguanide, the INN for which is polyhexanide. One example of a proprietary product including poly(hexamethylenebiguanide) is "Cosmocil CQ" (RTM) manufactured by Zeneca PLC.

The polybiguanide can be presented in the form of an acid addition salt, and examples of such salts include the salts formed with hydrochloric acid, sulphuric acid, phosphoric acid and acetic acid, a presently preferred salt being the hydrochloride.

The amount of polybiguanide, as defined above, is an effective preserving amount, i.e. an amount which is at least sufficient to preserve the solution. Thus the amount is at least sufficient to provide a biostatic effect, but preferably is an amount sufficient to have a biocidal effect. The amount of polybiguanide is generally selected so as to give at least a one log reduction in the level of microbial contaminants during five hours. More preferably the amount is selected so as to give at least a two log reduction in microbial contaminants over 5 hours. The concentration of the polybiguanide, for example poly (hexamethylenebiguanide), typically can be in the range of about 0.0001% to 0.1% w/v, and preferably is less than 0.1% w/v. More usually, the concentration will be in the range from about 0.0005% to 0.05% w/v. A particularly preferred concentration is approximately 0.002% w/v.

The type and amount of preservative are chosen such that whilst being active against non-viral microbial components of the vaccine process solutions, they do not adversely affect the ability of the virus to replicate or have an adverse effect on the quantities and properties of the viral antigens.

The method of the present invention is particularly applicable to enveloped viruses, i.e. viruses having a lipid bi-layer. Examples of such viruses include paramyxoviruses such as Sendai virus, orthomyxoviruses such as influenza viruses, toga viruses such as Semliki forest virus, and rhabdoviruses such as vesicular stomatitis virus.

In one preferred embodiment of the invention, there is provided a method of preventing or reducing bacterial contamination of an influenza vaccine during manufacture, which method comprises adding to a process solution containing influenza vaccine virus or influenza viral antigen (and in particular surface antigens such as haemaggiutinin and neuraminidase) an effective preserving amount of a polybiguanide.

The method of the invention is particularly useful for preventing microbial contamination of influenza vaccines of the "Fluvirin" type referred to above.

DETAILED DESCRIPTION OF PREFERRED EMBODIMENTS

Figure 1:
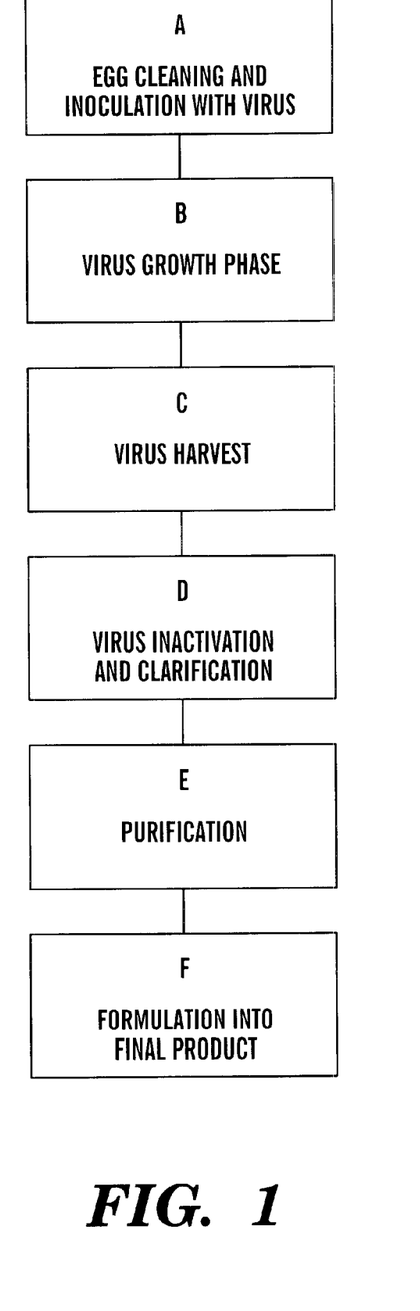
FIG. 1 illustrates a typical manufacturing process for an influenza vaccine.

Referring now to the figures, FIG. 1 illustrates a typical process for the preparation of influenza vaccine FIG. 1 illustrates schematically the sequence of steps involved in the manufacture of an influenza vaccine. Thus, chicken eggs are first washed to remove external contaminants and are then subjected to a primary incubation step (step A). Following the primary incubation, the eggs are inoculated with a dose of the desired viral strain (step A), and are then subjected to a secondary incubation step (step B) during which viral growth and multiplication takes place within the eggs. The allantoic fluid containing the virus is harvested from the eggs (step C). After harvesting, a preservative is added which, in accordance with the present invention, may be poly(hexamethylenebiguanide) at a concentration of between about 0.001 and 0.01% w/v (step C). The resulting preserved solution is clarified by centrifugation and. inactivated (step D) with a virus-inactivating agent.

Following inactivation, the solution is purified (step E) by standard methods and the purified viral fraction is then optionally treated with a further dose of poly (hexamethyienebiguanide) (step E) before the viral structures are disrupted by treating the fraction with a detergent to release the viral antigens. The resulting mixture can then be further purified and concentrated in accordance with standard techniques to give a solution containing the desired viral antigens. The purified antigens can then be blended as required with other batches of the same viral strain or with other strains to provide a polyvalent vaccine. The final product (step F) is then subjected to a series of quality control assays (step R) to measure such process parameters as the levels of haemagglutinin and neuraminidase antigens, residual viral activity, sterility, detergent levels and endotoxin levels.

During the course of the above process, and in particular during purification steps in which the antigen solutions are concentrated, the preservative typically is removed. Accordingly, unless fresh preservative is added at the filling stage, the final vaccine product filled into the syringes, ampoules or vials will contain minimal concentrations of the preservative. The addition of polybiguanide preservative, or indeed an alternative preservative at the filling stage could be desirable in relation to multidose vaccine compositions where there could otherwise exist the possibility of microbial contamination occurring between dispensing of first and last doses from the container.

Having described in general terms the vaccine production process, with particular reference to the production of influenza vaccine, the efficacy of polybiguanide compounds, and in particular poly(hexamethylenebiguanide), as preservatives for use in the process will now be illustrated by the following, non-limiting, examples.

EXAMPLE 1
Identification/comparison of Microbial Populations Contaminating Allantoic Fluid Fresh samples of allantoic fluid (approximately 100 mls) of preservative-free bulk harvest containing various influenza viral strains were taken and a 1 ml aliquot was diluted in 0.1% peptone and plated out in accordance with standard procedures. The bacterial species present in the fluid were then identified by standard procedures. The tests showed the presence of gram negative bacteria which were identified as being *Aeromonas hydrophila* or *Aeromonas caviae*, *Chromobacter violaceum*, *Enterobacter cloacae*, *Klebsiella* gr. 47, *Pseudomonas aeruginosa*, *Pseudomonas cepacia*, *Aeromonas salmonicida masarcida* or *Aeromonas achromogenes*, *Flavobacterium indologens*, *Pseudomonas stutzeri*, *Enterobacter agglomerans*, and *Flavobacterium meningosepticum*.

EXAMPLE 2
Comparison of Alternative Preservatives

Fresh samples of allantoic fluid containing influenza viral strains were divided into 100 ml volumes and were treated with one of the following preservatives at the solution strength indicated: thiomersal (0.01%), phenoxyethanol (1%), bronopol (0.1%) Biopure (0.4%), Nipaguard BPX (0.1%), polyhexamethylenebiguanide (Cosmocil CQ) (0.1% and 0.01%). The compositions of the preservatives other than thiomersal and phenoxyethanol are shown in Table 1 below.

TABLE 1

| Preservative | Active Component(s) | Manufacturer |
| --- | --- | --- |
| Cosmocil CQ | poly(hexamethylenebiguanide) hydrochloride (20%) | Zeneca |
| Nipaguard BPX | 5% bronopol*, 20% parabens 75% phenoxyethanol | Nipa Laboratories |
| Nipaguard BNPD | 99% bronopol | Nipa Laboratories |
| Biopure | 43% imidazolidinyl urea | Nipa Laboratories |
| Myacide Pharma | 99% bronopol | Knoll Microcheck |

*bronopol is 2-bromo-2-nitropropan-1,2-diol

Figure 2:
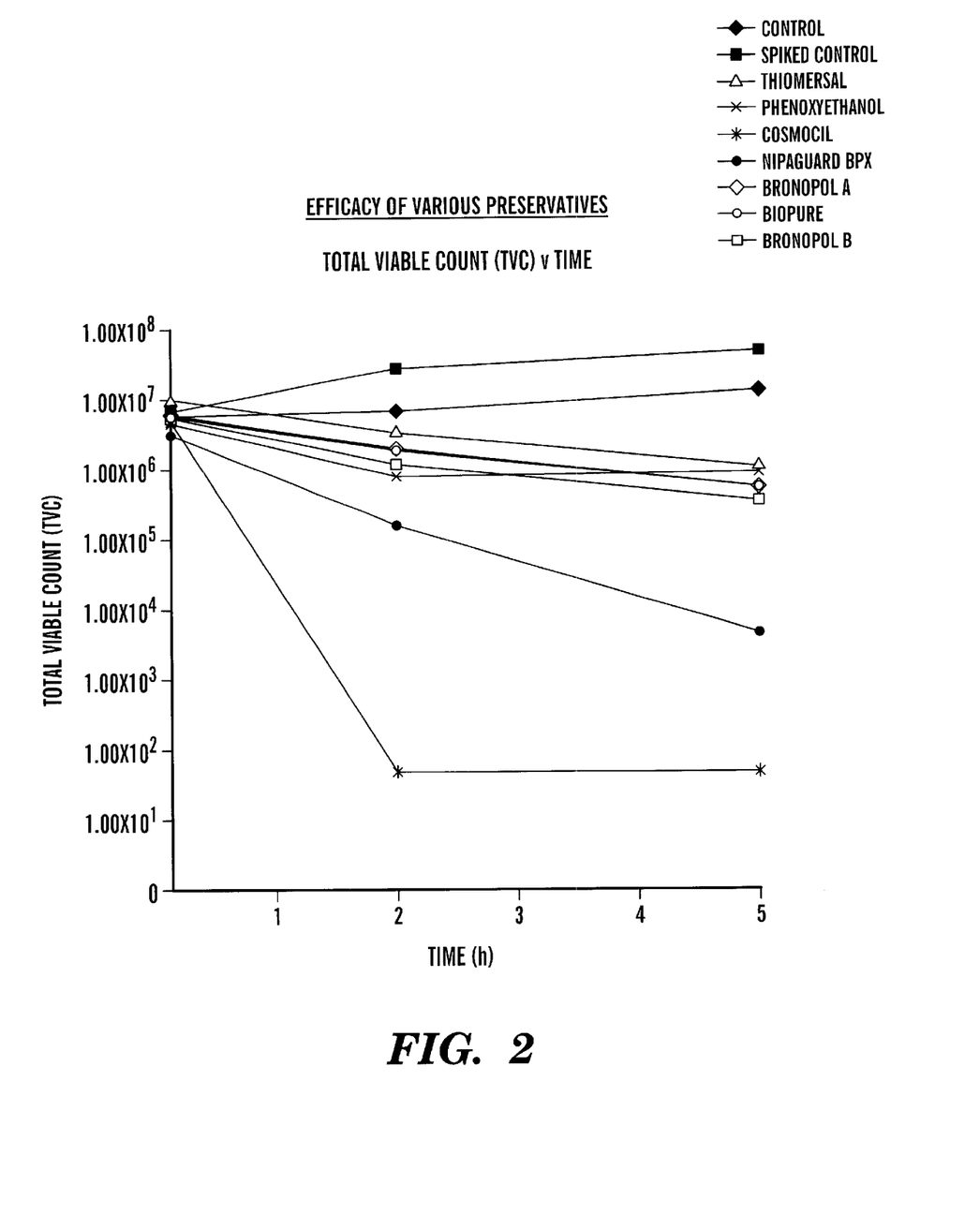
FIG. 2 illustrates the preservative efficacy of poly (hexamethylenebiguanide) (Cosmocil CQ) relative to other preservatives.
Figure 3:
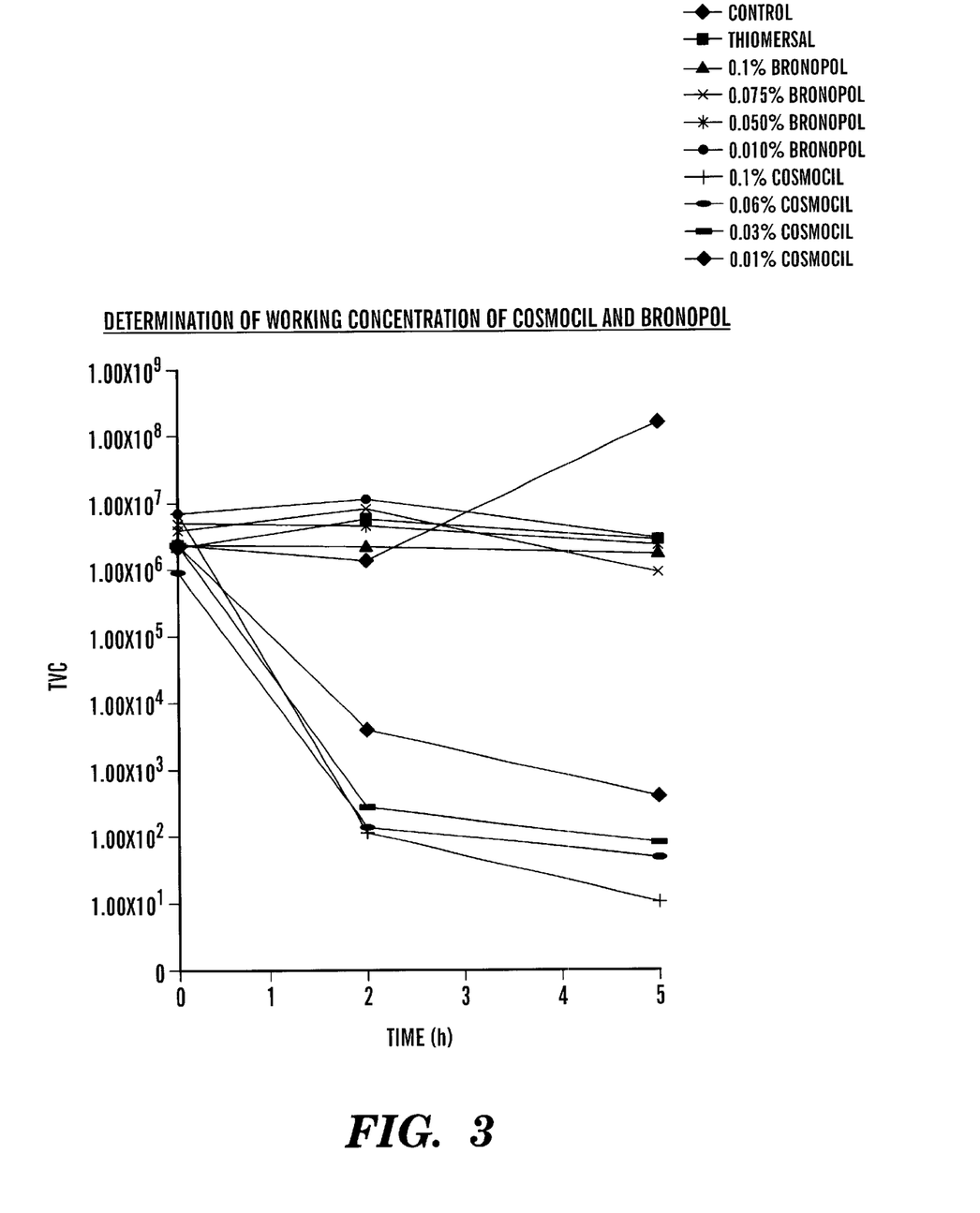
FIG. 3 illustrates the preservative efficacy of different concentrations of Cosmocil CQ in comparison to thiomersal and bronopol.
Figure 4:
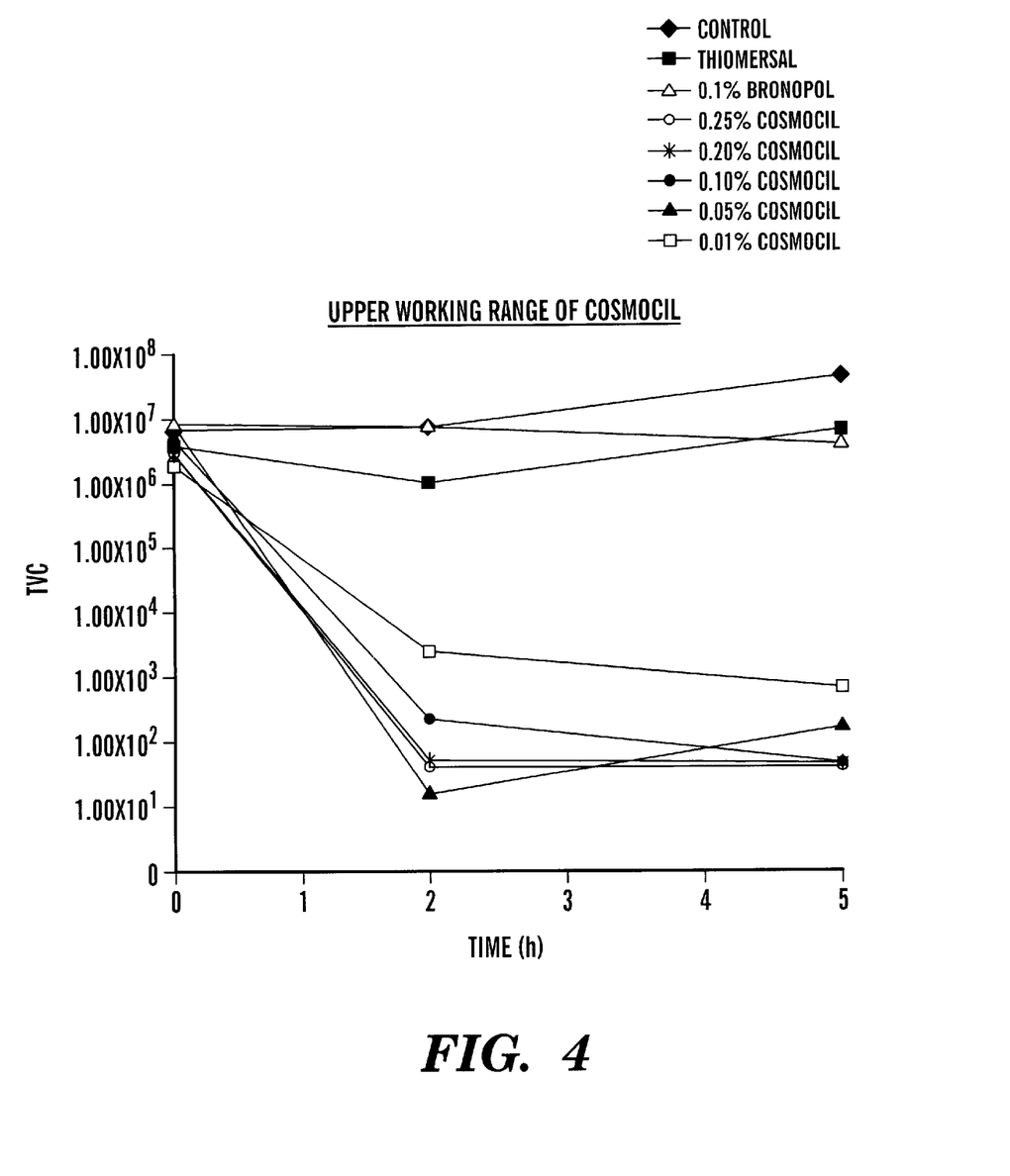
FIG. 4 is a plot of total viable count against time for different concentrations at the upper end of the working range for Cosmocil CQ.
Figure 5:
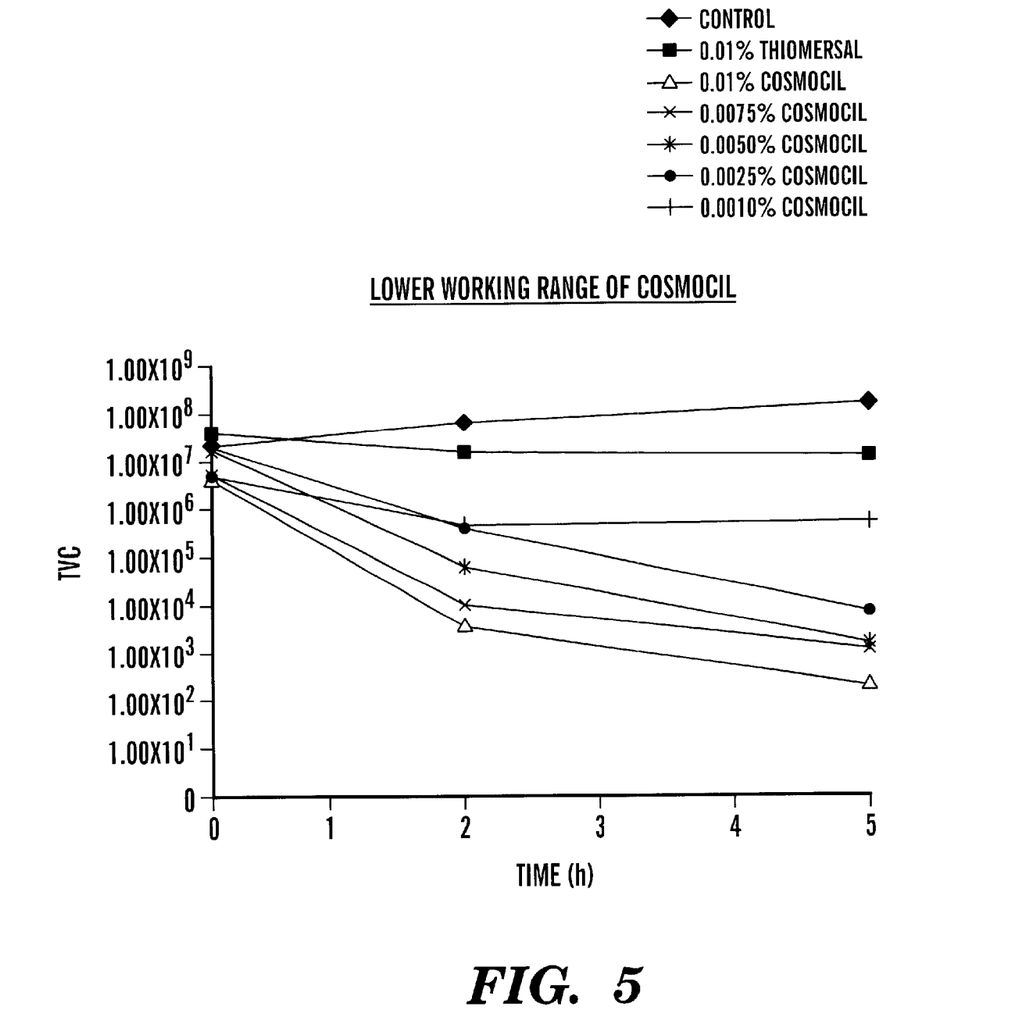
FIG. 5 is a plot of total viable count against time for concentrations of Cosmocil CQ at the lower end of its working range.

The total viable counts for each of the solutions tested, along with a control solution and a spiked control solution (1 ml of *P. aeruginosa* containing $8 \times 10^8$ CFU/ml—in 100 ml of allantoic fluid) are shown in Table 2 below and in FIG. 2.

The results are summarised in Table 3 below.

TABLE 3

| Preservative | Level of Contamination Log values (5 hours treatment) | Approx. Log Reduction |
| --- | --- | --- |
| thiomersal (0.01%) | 6.0 | 1 |
| phenoxyethanol (1%) | 5.5 | 1.5 |
| bronopol (0.1%)** | 5.0 | 2 |
| Biopure (0.4%) | 5.0 | 2 |
| Nipaguard BPX (0.1%) | 3.0 | 4 |
| Cosmocil CQ (0.1%) | 1.0 | 6 |
| Cosmocil CQ (0.001%) | 2.0 | 5 |

**Results similar for both Bronopol formulations.

The results show that Cosmocil CQ at 0.1% (v/v) performed better than all the other preservatives. Nipaguard BPX was the second most effective preservative followed in order of descending efficacy by bronopol (Myacide Pharma BP), Biopure, bronopol (Nipaguard BNPD), phenoxyethanol and thiomersal. Thiomersal, Biopure, and phenoxyethanol behaved as biostatic preservatives. The remaining preservatives were biocidal and resulted in slower growing colonies even after sub-culture.

The preserved samples were also examined to determine the visible effect on allantoic fluid, and the results are shown in Table 4 below.

TABLE 4

| Preservative | Effect on allantoic fluid (visible) |
| --- | --- |
| 0.1% Cosmocil CQ | Slight precipitate |
| 0.4% Nipaguard BPX | Heavy Precipitate. Poor Solubility |
| 0.1% Nipaguard BNPD (bronopol) | No effect |
| 0.1% Myacide Pharma BP (bronopol) | No effect |
| 1.0% phenoxyethanol | Heavy precipitate. Poor solubility |
| 0.4% Biopure | No effect |

EXAMPLE 2
Effect of Selected Preservatives on Egg Infectivities and Surface Antigens In order to determine the effect of each preservative on the growth of virus within the egg, egg infectivity assays were carried out to compare the properties of thiomersal, polyhexamethylenebiguanide (Cosmocil CQ), bronopol and Biopure. The seed virus/preservative compositions were made as follows with appropriate dilutions of the preservatives made up in phosphate buffered saline at Ph 7.2.

1. Untreated control (1 ml seed virus)
2. Virus seed (1 ml)+0.01% thiomersal
3. Virus seed (1 ml)+0.1% Cosmocil CQ

TABLE 2

| T (hr) | Control | Spiked control | Thiomersal | Phenoxy- ethanol | Nipaguard BPX | Nipaguard BNPD | Cosmocil CQ | Biopure | Myacide Pharma |
| --- | --- | --- | --- | --- | --- | --- | --- | --- | --- |
| 0 | $5.90 \times 10^6$ | $6.40 \times 10^6$ | $9.60 \times 10^6$ | $4.10 \times 10^6$ | $3.00 \times 10^6$ | $5.20 \times 10^6$ | $5.00 \times 10^6$ | $6.10 \times 10^6$ | $5.20 \times 10^6$ |
| 2 | $6.70 \times 10^6$ | $2.60 \times 10^7$ | $3.20 \times 10^6$ | $8.20 \times 10^5$ | $1.70 \times 10^5$ | $2.00 \times 10^6$ | $5.00 \times 10^1$ | $1.80 \times 10^6$ | $1.10 \times 10^6$ |
| 5 | $1.20 \times 10^7$ | $5.10 \times 10^7$ | $1.20 \times 10^6$ | $9.40 \times 10^5$ | $5.00 \times 10^3$ | $5.50 \times 10^5$ | $5.00 \times 10^1$ | $5.50 \times 10^5$ | $3.80 \times 10^5$ |

4. Virus seed (1 ml)+0.1% bronopol (Nipaguard)

5. Virus seed (1 ml)+0.4% Biopure

Each of the above compositions was used to inoculate 10 eggs which were then incubated and chilled in the normal manner, following which the viral concentrations were determined by the number of eggs causing haemagglutination of chick red blood cells according to the Karber formula (see Virological Technique, by Busby et al. Publ. J & A Churchill Ltd, London, (1964), pp 146–147). The results are shown in Table 6 below.

TABLE 6

|  | Untreated control | 0.01% Thiomersal | 0.1% Cosmocil CQ | 0.1% Bronopol | 0.4% Biopure |
| --- | --- | --- | --- | --- | --- |
| Log egg infective doses/ml | 9.2 | 8.2 | 8.9 | <5.4 | <5.4 |

The results illustrate that bronopol and Biopure had a pronounced negative effect on egg infectivities compared with Cosmocil CQ and thiomersal.

In order to determine the effect of various preservatives on influenza surface antigens, a single radial diffusion assay (an immunodiffusion technique) was used to determine haemagglutinin (HA) concentrations in a purified surface antigen monoblend (derived from Influenza B Harbin) to which the preservative had been added. The results are shown in Table 6 below.

TABLE 6

| | Untreated control | 0.01% Thiomersal | 0.1% Cosmocil CQ | 0.1% Bronopol | 0.4% Biopure |
|---|---|---|---|---|---|
| HA conc'n (μg/ml) | 20.85 | 25.15 | 20.15 | 20.46 | 23.53 |

The results of the assays show that none of the preservatives tested had any obvious effect on the HA levels of the vaccine.

An enzyme linked immunosorbent assay (ELISA) was carried out to determine neuraminidase levels in purified surface antigen monoblend solutions derived from allantoic fluid to which preservatives had been added at the initial harvesting stage. The results are shown in Table 7 below.

TABLE 7

| Absorbances | Untreated control | 0.01% Thiomersal | 0.1% Cosmocil CQ | 0.1% Bronopol | 0.4% Biopure |
|---|---|---|---|---|---|
| Dilution 1/500 | 0.773 | 0.780 | 1.629 | 0.760 | 0.769 |
| Dilution 1/2000 | 0.807 | 0.784 | 0.955 | 0.779 | 0.785 |
| Dilution 1/8000 | 0.773 | 0.739 | 0.783 | 0.764 | 0.765 |

The results of the assays showed that Cosmocil CQ caused interference with the assay at higher concentrations but very little interference at lower concentrations. This interference does not affect the neuraminidase content of the vaccine.

Electron microscopic investigations were also carried out to demonstrate the effect of varying concentrations of polyhexamethylenebiguanide (Cosmocil CQ) on clumping of A/Nanchang Influenza particles. The results of the clumping assays and the other analytical assays carried out on the purified surface antigen monoblend, are summarised in Table 8 below.

TABLE 8

| Assay | 0.1% Cosmocil CQ | 0.01% Cosmocil CQ | 0.4% Biopure | 0.1% Bronopol |
|---|---|---|---|---|
| Infectivities | Satisfactory | Satisfactory | Unsatisfactory | Unsatisfactory |
| SRD | Satisfactory | Satisfactory | Satisfactory | Satisfactory |
| Neuraminidase | Assay Interference | Slight Assay interference | Satisfactory | Satisfactory |
| Electron Microscopy | Clumping | Satisfactory | Not carried out | Not carried out |

Experiment 4

Determination of the Effect of Different Concentrations of Polyhexamethylenebiguanide (Cosmocil CQ) and Bronopol Bronopol and polyhexamethylenebiguanide (Cosmocil CQ) were added at differing concentrations to samples of allantoic fluid harvested from influenza A/Texas strain, and the total viable counts for each treated solution checked at 2 and 5 hours. The results are shown in FIG. 3. The results illustrate that bronopol and thiomersal have a bacteriostatic effect on bacterial populations whereas the Cosmocil CQ is biocidal. The different concentrations of Cosmocil CQ behaved similarly giving final total viable counts of between $1\times10^2$ to $3.9\times10^3$ microorganisms for 0.1 and 0.01% Cosmocil CQ respectively. A small amount of cloudy precipitate was observed in the 0.1% and 0.06% Cosmocil CQ treated samples. The level of cloudiness decreased with Cosmocil CQ concentration and was virtually undetectable at 0.01%. It is noteworthy that this precipitation did not occur with the Influenza A/Nanchang strain.

Further studies were carried out to determine the upper and lower working concentrations of Cosmocil CQ. For this purpose, concentrations were taken at 9 percentage points between 0.001% and 0.1%. Bronopol at 0.1% was also included as a reference sample The results are shown in FIG. 4.

As can be seen from FIG. 4, all concentrations of Cosmocil CQ between 0.01% and 0.25% behave in a similar manner. A slight precipitation was again observed for higher concentrations of Cosmocil CQ. These results confirm that 0.01% Cosmocil CQ is preferable to 0.1% Cosmocil CQ. The Cosmocil CQ concentrations between 0.001% and 0.01% all gave better results than the thiomersal. The results thus indicate that Cosmocil CQ can be used successfully at concentrations ten times lower than thiomersal.

The results suggest that a concentration of 0.01% Cosmocil CQ (which equates to 0.002% polyhexamethylenebiguanide) is optimal on the basis that (a) it reduces viable counts by three to four log units, (b) it does not cause clumping of the virus and other allantoic fluid components and so is unlikely to interfere with the manufacturing process and (c) it should be capable of coping with unexpectedly high levels of bacteria should they occur.

The invention has been illustrated by reference to a particular viral vaccine and a particular polybiguanide, but it is anticipated that the use of the exemplified polybiguanide and other polybiguanides would find use in the manufacture of other viral vaccines, particularly those obtained from other enveloped viruses such as paramyxoviruses (e.g. Sendai virus), other orthomyxoviruses, toga viruses (e.g. Semliki forest virus), and rhabdoviruses (e.g. vesicular stomatitis virus).

We claim:

1. A method of preventing or reducing bacterial contamination of a viral vaccine, said method comprising adding an effective preserving amount of a preservative composition containing a polybiguanide to a solution containing vaccine virus or virus antigen, wherein the polybiguanide is a polymeric compound comprising a plurality of repeating units, each repeating unit being represented by the formula:

—[NH—C(NH)—NH—C(NH)—NH—R]$_n$— wherein R is a divalent hydrocarbon chain and the value of n in each repeating unit is in the range from 2 to 40.

2. A method according to claim 1 wherein the solution containing vaccine virus or virus antigen is a final form of the vaccine immediately prior to or after filling into a dosage container.

3. A method according to claim 1 wherein the solution containing vaccine virus or virus antigen is a process solution.

4. A method of preventing or reducing bacterial contamination of a viral vaccine during manufacture of the vaccine, said method comprising adding an effective preserving amount of a preservative composition containing a polybiguanide to a process solution containing vaccine virus or virus antigen, wherein the polybiguanide is a polymeric compound comprising a plurality of repeating units, each repeating unit being represented by the formula:

—[NH—C(NH)—NH—C(NH)—NH—R]$_n$— wherein R is a divalent hydrocarbon chain and the value of n in each of said repeating units is in the range from 2 to 40.

5. A method according to claim 3 wherein the process solution is chosen from the group consisting of:

(a) a viral growth medium to which the vaccine virus has been added or is subsequently added;

(b) a solution of virus harvested from the medium in which the virus has been grown;

(c) a solution containing disrupted virus and free antigens: and (d) partially purified and purified solutions of antigens.

6. A method according to claim 4 wherein the process solution is chosen from the group consisting of:

(a) a viral growth medium to which the vaccine virus has been added or is subsequently added;

(b) a solution of virus harvested from the medium in which the virus has been grown;

(c) a solution containing disrupted virus and free antigens (d) partially purified and purified solutions of antigens.

7. A method according to claim 1 wherein the polybiguanide contains a mixture of molecules of differing chain lengths, each molecule comprising a plurality of repeating units, each repeating unit being represented by the formula:

—[NH—C(NH)—NH—C(NH)—NH—R]$_n$— wherein R is a divalent hydrocarbon chain and the value of n in each of said repeating units is in the range from 2 to 40 and wherein the value of n may differ between molecules.

8. A method according to claim 7 wherein the average value of n is in the range from 3 to 20.

9. A method according to claim 8 wherein the average value of n is in the range from 4 to about 16.

10. A method according to claim 1 wherein the polybiguanide has a molecular weight, excluding the weight of any acid present in the form of acid addition salts of the polybiguanide, of up to 12,000.

11. A method according to claim 10 wherein the polybiguanide is poly(hexamethylene) biguanide.

12. A method according to claim 1, wherein the polybiguanide is in the form of a hydrochloride salt.

13. A method according to claim 1, wherein the concentration of polybiguanide is such as to give at least a one log reduction in the level of microbial contaminants during five hours.

14. A method according to claim 13, wherein the concentration of polybiguanide is such as to give at least a two log reduction in microbial contaminants over 5 hours.

15. A method according to claim 1 wherein the concentration of the polybiguanide is in the range of about 0.0001% to 0.1% w/v.

16. A method according to claim 1 wherein the vaccine virus is an enveloped virus.

17. A method according to claim 16 wherein the vaccine virus is Sendai virus or an orthomyxovirus.

18. A method according to claim 17 wherein the vaccine virus is an orthomyxovirus which is influenza virus.

19. A method of preventing or reducing bacterial contamination of an influenza vaccine during manufacture, said method comprising adding an effective preserving amount of a polybiguanide to a process solution containing influenza vaccine virus or influenza viral antigen, wherein the polybiguanide is a polymeric compound comprising a plurality of repeating units, each repeating unit being represented by the formula:

—[NH—C(NH)—NH—C(NH)—NH—R]$_n$— wherein R is a divalent hydrocarbon chain and the value of n in each of said repeating units is in the range from 2 to 40.

20. A method of preventing or reducing bacterial contamination of a viral vaccine with one or more bacterial species selected from the group consisting of *Aeromonas hydrophila, Aeromonas caviae, Chromobacter violaceum, Enterobacter cloacae,* Klebsiella gr.47, *Pseudomonas aeruginosa, Pseudomonas cepacia, Aeromonas salmonicida masarcida* or *Aeromonas achromogenes, Flavobacterium indologens, Pseudomonas stutzeri, Enterobacter agglomerans,* and *Flavobacterium meningosepticum;* the viral vaccine being one which is produced using eggs as a viral growth medium; said method comprising adding an effective preserving amount of a preservative composition containing a polybiguanide to a solution containing vaccine virus or virus antigen, wherein the polybiguanide is a polymeric compound comprising a plurality of repeating units, each repeating unit being represented by the formula:

$$-[NH-C(NH)-NH-C(NH)-NH-R]_n-$$

wherein R is a divalent hydrocarbon chain and the value of n in each of said repeating units is in the range from 2 to 40.

21. A method according to claim 20, wherein the solution containing a vaccine virus or virus antigen is one which is contaminated by one or more of said bacterial species.

22. A preserved viral vaccine composition comprising a solution containing vaccine virus or virus antigen and an effective preserving amount of a preservative composition containing a polybiguanide, wherein the polybiguanide is a polymeric compound comprising a plurality of repeating units, each repeating unit being represented by the formula:

$$-[NH-C(NH)-NH-C(NH)-NH-R]_n-$$

wherein R is a divalent hydrocarbon chain and the value of n in each of said repeating units is in the range from 2 to 40.

23. A preserved viral vaccine composition according to claim 22 wherein the polybiguanide contains a mixture of molecules of differing chain lengths, each molecule comprising a plurality of repeating units, each repeating unit being represented by the formula:

$$-[NH-C(NH)-NH-C(NH)-NH-R]_n-$$

wherein R is a divalent hydrocarbon chain and the value of n in each of said repeating units is in the range from 2 to 40 and wherein the value of n may differ between molecules.

24. A preserved viral vaccine composition according to claim 23 wherein the average value of n is in the range from 3 to 20.

25. A preserved viral vaccine composition according to claim 24 wherein the average value of n is in the range from 4 to about 16.

26. A method according to claim 19 wherein the polybiguanide contains a mixture of molecules of differing chain lengths, each molecule comprising a plurality of repeating units, each repeating unit being represented by the formula:

$$-[NH-C(NH)-NH-C(NH)-NH-R]_n-$$

wherein R is a divalent hydrocarbon chain and the value of n in each of said repeating units is in the range from 2 to 40 and wherein the value of n may differ between molecules.

27. A method according to claim 26 wherein the average value of n is in the range from 3 to 20.

28. A method according to claim 27 wherein the average value of n is in the range from 4 to about 16.

* * * * *